United States Patent
Wiley

(10) Patent No.: US 8,622,962 B1
(45) Date of Patent: Jan. 7, 2014

(54) SAFETY SYRINGE AND METHOD FOR USING THE SAME

(75) Inventor: Christopher W. Wiley, Hanover, NH (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 590 days.

(21) Appl. No.: 12/501,848

(22) Filed: Jul. 13, 2009

Related U.S. Application Data

(60) Provisional application No. 61/080,614, filed on Jul. 14, 2008.

(51) Int. Cl.
*A61M 5/00* (2006.01)

(52) U.S. Cl.
USPC ............ 604/111; 604/110; 604/218; 604/228

(58) Field of Classification Search
USPC ......... 604/110, 111, 118, 121, 218, 220, 227, 604/228
See application file for complete search history.

(56) References Cited

U.S. PATENT DOCUMENTS

| 4,759,750 A | 7/1988 | DeVries |
| 6,866,648 B2 | 3/2005 | Hadzic |
| 2007/0191785 A1 * | 8/2007 | Barere et al. ................. 604/228 |

OTHER PUBLICATIONS

Hadzic, "Combination of Intrneural Injection and High Injection Pressure Leads to Fascicular Injury and Neurologic Deficits in Dogs", , pp. 417-723, vol. 29, No. 5, Publisher: Regional Anesthesia and Pain Medicine, Published in: US.

* cited by examiner

*Primary Examiner* — Kami A Bosworth
(74) *Attorney, Agent, or Firm* — Loginov & Sicard; Keri E. Sicard; William A. Loginov

(57) ABSTRACT

A safety syringe that effectively prevents the administration of an injection in excess of a maximum injection pressure, and that provides a clear, immediate tactile feedback to the practitioner each time a maximum injection pressure is exceeded. The practitioner is provided a predetermined number of attempts to inject fluid without exceeding the maximum injection pressure, each time receiving a direct tactile feedback in the form of a ratcheting click within the plunger assembly of the syringe. After a final attempt, the next overpressure event causes a disconnect between the thumb plate of the syringe and the piston that engages the fluid within the syringe barrel, positively prevent a potentially harmful injection. In an illustrative embodiment, the plunger assembly includes a distal portion connected to the piston and a proximal portion, connected to the thumb plate.

16 Claims, 8 Drawing Sheets

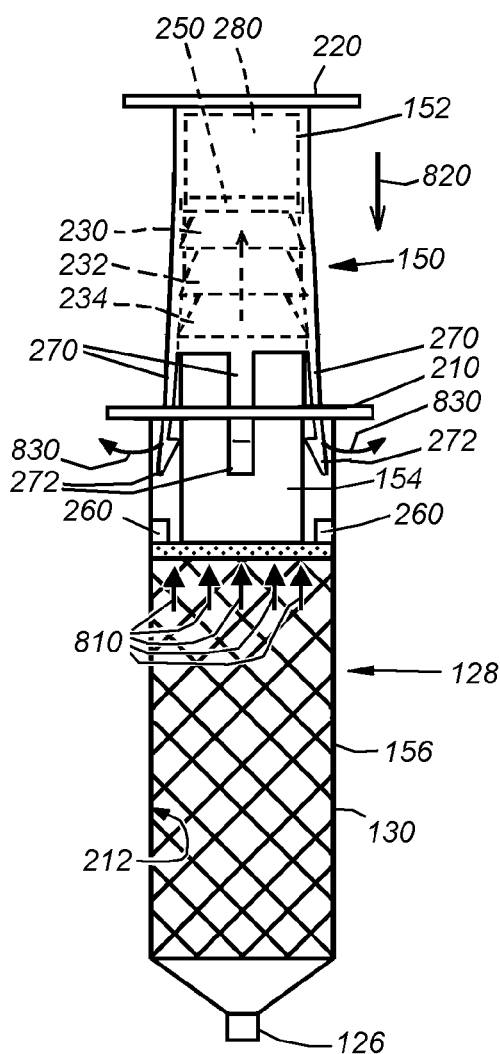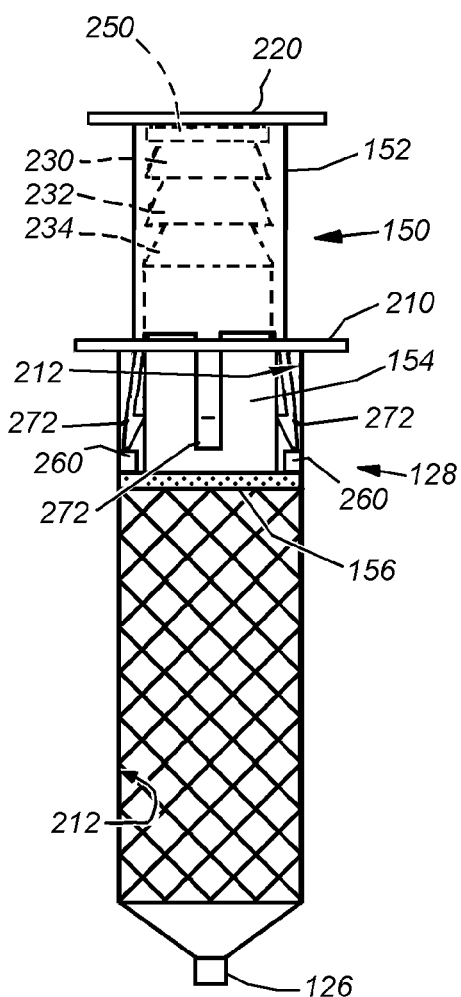
*Fig. 8*  *Fig. 9*

SAFETY SYRINGE AND METHOD FOR USING THE SAME

RELATED APPLICATIONS

This application claims the benefit of U.S. Provisional Patent Application Ser. No. 61/080,614, filed Jul. 14, 2008, entitled SAFTEY SYRINGE AND METHOD FOR USING THE SAME, the entire disclosure of which is herein incorporated by reference.

FIELD OF THE INVENTION

This invention relates to hypodermic medical syringes, and more particularly to medical syringes adapted to prevent over-pressurized administration of fluids.

BACKGROUND OF THE INVENTION

Peripheral nerve blocks are performed by injecting local anesthetic solution very near, but not inside, major nerves or plexuses. When properly performed, these blocks can provide surgical anesthesia and/or postoperative pain relief. General anesthesia and/or narcotics can often be avoided or minimized, thus reducing potential side effects. Unfortunately, if the local anesthetic is mistakenly injected inside the nerve, rather than next to it, the result can be permanent nerve damage.

Various techniques and technologies have evolved over the past century in an effort to improve the success and safety of regional anesthesia. Blind techniques, relying on paresthesias or "clicks and pops" being sensed by the practitioner as the needle is inserted, were supplanted by the use of peripheral nerve stimulation to elicit a motor response when the block needle approached the nerve. In turn, nerve stimulation is now being replaced in many treatment centers by direct visual guidance using high-frequency ultrasound. While ultrasound guidance has greatly improved the speed and reliability of peripheral blocks, the possibility of intraneuronal injection with permanent catastrophic neuropathy still remains a concern. For example, if the block needle is angled slightly relative to the ultrasound beam, its tip may fall outside the beam, and not be visible as it enters a nerve. Dr. Admir Hadzic and colleagues have shown that it is actually injection pressure that determines whether or not a nerve will be damaged by intraneuronal injection (Reg. Anesth. Pain Med. 2004; 29:417-423). Specifically, it was determined that it is unsafe to exceed 20 psi during the injection. Injection pressures below that threshold failed to damage the nerves, even when the needle had penetrated the wall, and was definitely inside the nerve at the time of injection.

U.S. Pat. No. 6,866,648, entitled METHOD AND APPARATUS TO DECREASE THE RISK OF INTRANEURONAL INJECTION DURING ADMINISTRATION OF NERVE BLOCK ANESTHESIA, by Dr. Admir Hadzic, et al., the teachings of which are expressly incorporated herein by reference, describes a system for more safely administering injections using a syringe that incorporates a "pop-up" valve assembly in line with the injection tubing and associated fluid path. The valve pops up to provide a visual cue that a predetermined safe injection pressure has been exceeded. A version of this device is marketed under the name BSMART™ by Concert Medical LLC, Norwell, Mass. While this device is useful—particularly in raising awareness as to the need for a safety-injection system, it possesses at least two significant shortcomings. First, the pop-up valve must be continually observed by the practitioner while the injection is being made. This is not practical in a real-world clinical setting. Rather, distractions are possible in any setting, and with the use of ultrasound guidance all eyes tend to be on the ultrasound screen—not the syringe. Second, while the Hadzic device may indicate excessive pressure during the injection, it does not prevent it. The danger of permanent nerve damage, while reduced, still remains completely in the hands of the practitioner.

Another earlier attempt to provide a safety syringe is disclosed in U.S. Pat. No. 4,759,750, entitled PRESSURE SENSING SYRINGE, by James H. DeVries, et al., the teachings of which are expressly incorporated herein by reference. This device provides a pop-up projection within the center of the syringe plunger thumb plate. This projection is biased through the thumb plate, and painlessly into the practitioner's thumb, if the injection pressure fed-back though the syringe barrel exceeds a predetermined level. Thus, this device avoids the disadvantageous requirement that the practitioner split his or her attention between the syringe and the ultrasound display as encountered in Hadzic by providing a tactile, rather than a visual, indicator of excess injection pressure. However, this device also fails to prevent an over-pressurized injection. In addition, different practitioners' sensitivity and response time to an over-pressure indication may vary widely. Some practitioners may simply not feel the indicator, or only feel it after significant over-pressure has occurred—particularly through thickened surgical gloves.

It is, therefore, desirable to provide a safety syringe, applicable to the administration of neural blocks and other forms of hypodermic injection, which provides a tactile indication of an injection pressure that exceeds a predetermined level. It is further desirable that the safety syringe allow the practitioner to maintain visual attention of the injection site and/or an imaging display of the site, such as employed in ultrasound device. Moreover, it is desirable to provide a safety syringe system, and method for using such a system, which actively prevents the administration of an injection that exceeds a predetermined fluid pressure. The system should be adapted so that the fluid pressure limit is variable for differing types of injections/syringes, and should be easily manufactured, facilitating its use as a generally disposable item.

SUMMARY OF THE INVENTION

This invention overcomes the disadvantages of the prior art by providing a safety syringe that effectively prevents the administration of an injection in excess of a maximum injection pressure, and that provides clear, immediate tactile feedback to the practitioner each time a maximum injection pressure is exceeded. The practitioner is provided a predetermined number (three in one example) attempts to inject fluid without exceeding the maximum injection pressure, each time receiving a direct tactile feedback in the form of a ratcheting click within the plunger assembly of the syringe if the maximum pressure is exceeded. After a final attempt, the next over-pressure event causes a disconnect between the thumb plate of the syringe and the piston that engages the fluid within the syringe barrel, positively preventing a potentially harmful injection. In an illustrative embodiment, the plunger assembly includes a distal portion connected to the piston and a proximal portion, connected to the thumb plate. The distal portion and the proximal portion are interconnected via a ratcheting mechanism constructed of spring loaded pawls on one section and conforming ramps, arranged as a series of steps on the other section. The ramps can be externally located on the section or internally located. The distal-most ramp leads to a sliding section that elastically deforms the spring structures that carry the pawls (unitarily molded leaf-spring arms for example), and allows the pawls to slide, relatively free of resistance so that the two sections become disconnected from each other. A stop prevents the proximal section from hereafter sliding distally into engagement with the distal section. The stop can be the proximal end of the barrel itself, or can be an internally located abutment within the barrel that engages distal ends of arms after they have been elastically deformed in a radially outward direction by the disconnection mechanism—the arms normally sliding past the internal abutment when not deformed.

In various embodiments, the arm assembly can comprise a plurality of circumferentially separated, individual leaf springs and pawls that depend from the proximal portion. Alternatively the arm assembly can comprise a unitary rim that deforms to jump from one ramp to another by a hoop stress generated as a result of the force differential between the proximal and distal sections. In various embodiments, an additional guiding structure, such as a central guide rod can be provided on one of the sections and communicate with a channel on another of the sections to maintain alignment therebetween, and alleviating a bending moment as the proximal section delivers driving force to the distal section.

BRIEF DESCRIPTION OF THE DRAWINGS

The invention description below refers to the accompanying drawings, of which:

FIG. 8 is an exposed side view of the safety syringe as shown in FIG. 2, with the plunger assembly located in a position prior to administration of an injection following a third unsuccessful attempt in which the predetermined injection pressure is exceeded;

FIG. 9 is an exposed side view of the safety syringe as shown in FIG. 8, wherein the plunger assembly becomes configured so as to prevent further attempts at administration of the injection;

DETAILED DESCRIPTION

Figure 1:
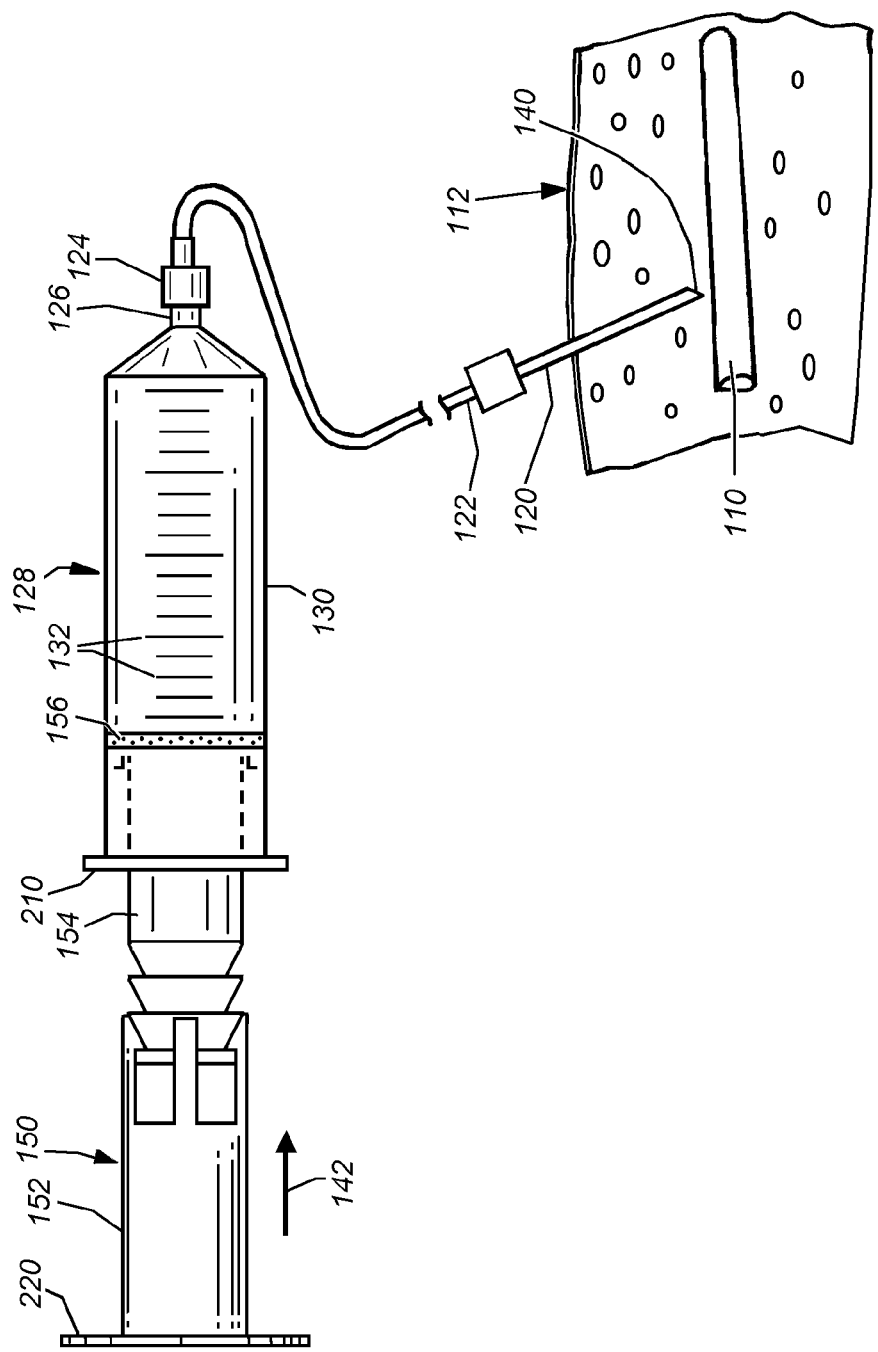
FIG. 1 is an exposed diagram of a safety syringe system administering a neural block according to an illustrative embodiment of the invention.

FIG. 1 details, by way of example, the administration of a peripheral nerve block with respect to a target nerve 110 beneath body tissue 112 according to an illustrative embodiment of this invention. In the depicted embodiment, the nerve is provided with a local anesthetic using a hypodermic needle 120 sized and arranged for that task. The needle 120 is mounted on, and in fluid-communication with, the distal end of an elongated tubing 122. The opposing proximal end of the tubing 122 is fitted, using a proximal fitting 124, to the distal end 126 of an illustrative syringe 128 according to an embodiment of this invention.

In operation, the practitioner fills the transparent/translucent barrel 130 of the syringe 128 with an appropriate volume of anesthetic or another solution. The barrel 130 can include the depicted volumetric gradations 132 that allow for metering of the appropriate amount of solution prior to attachment of the tubing 122 and/or needle 120. The anesthetic is directed pressurably from the distal end 124 of the needle 140 by pressing (in a distal direction as shown by arrow 142) of a syringe's plunger assembly 150. As will be described below, the plunger assembly 150 can be constructed in a variety of sizes, shapes and geometries. In general, the plunger assembly 150 consists of a proximal plunger section 152 that is engaged by a thumb or other portion of the practitioner's hand, and an interconnected distal plunger section 154 that includes a distal plunger end or piston 156 that moves slidably within the barrel 130 in a manner that maintains a seal with respect to the inner wall of the barrel.

As described generally above, it has been recognized by research that, in most cases, even when the needle's distal end 140 pierces a nerve 110, actual damage is not typically caused by the piercing action, but by excess fluid pressure building rapidly within the interior of the nerve. Nerves are, in fact, bundles of neurons formed into individual vesicles. When the outer sheath of a nerve is pierced, the needle tends to travel into the space between vesicles. The vesicles itself may tend to move aside rather than rupturing as the needle passes, thereby protecting the more delicate neuron structure inside each vesicle. However, when injected fluid pressure exceeds a predetermined level, it tends to fill the region of the nerve around the needle without a rapid means of escape. This excess pressure can, in essence, constrict and deprive the vesicles of needed blood flow. This condition causes actual nerve damage. Below a predetermined pressure, the nerves retain their ability to receive sufficient blood flow until the local pressure is relieved by seepage of the infused fluid into surrounding tissues. Hence, the plunger assembly 150 according to the various embodiments of this invention, to be described below, is constructed and arranged to ensure the practitioner does not inject fluid beyond a predetermined, maximum allowable injection pressure. In accordance with illustrative embodiments relating to peripheral nerve block syringes, this maximum injection pressure is set to approximately 20 psi or less.

It should be appreciated that the safety syringe according to the various embodiments of this invention (to be described in further detail below) can be applied to other areas of the body and other forms of treatment in addition to the exemplary nerve blocks, where the maximum pressure may be set at another predetermined level—for example, the eye or an internal organ.

In the case of a peripheral nerve block application of the illustrative safety syringe, it is contemplated that any pressure in excess of 20 psi, caused either an overly aggressive attempt at injection into normal tissue by the practitioner, or more likely, an attempt to inject fluid into a region that resists introduction of such fluid. In particular, the interior of a nerve will tend to resist rapid introduction of fluid and thus, even injections at a normal flow rate will be resisted by a resulting backpressure. More particularly, attempts to inject fluid at a normal flow rate into the interior of a nerve will generally require pressures in excess of 20 psi. The functionality of the illustrative safety syringe is such that attempts to inject fluid that meet resistance above a predetermined maximum pressure will cause the novel plunger assembly 150 of this embodiment to deliver an immediate, and unmistakable tactile response, thereby placing the practitioner on notice that the injection site is improper. Repeated failed injection attempts by the practitioner, which exceed the maximum injection pressure, will eventually lead to complete lock-up of the plunger assembly without the ability to further inject fluid effectively preventing harm to the injection site.

Figure 2:
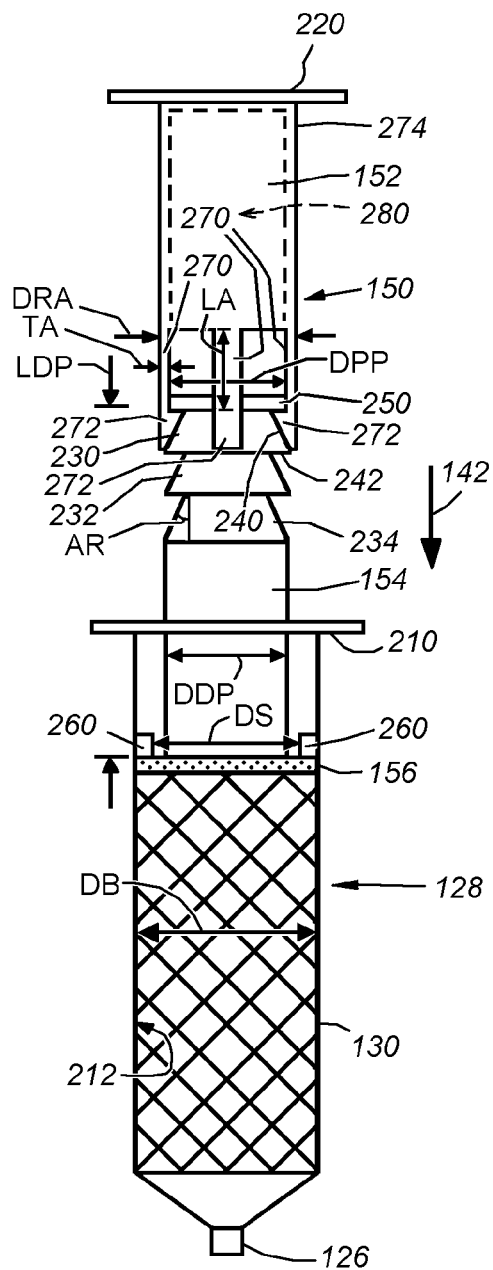
FIG. 2 is a an exposed side view of the safety syringe according to FIG. 1 with the plunger assembly located in a position prior to administration of an injection.

Reference is now made to FIGS. 2-9, which show the first illustrative embodiment of the safety syringe 128 in various stages of operation. Referring to FIG. 2, the plunger assembly 150 of the safety syringe 128 is shown fully withdrawn proximally, ready to inject the fluid contents of the barrel 130. The barrel 130 in this embodiment is transparent or translucent, exposing the fluid contents of the syringe 128 and the components of the plunger assembly 150 to the practitioner, as shown. The barrel 130 includes a flange 120, which can be any appropriate size and/or shape to assist the practitioner in supporting the barrel during the injection procedure. The barrel 128 includes a smooth inner wall 212 that slidably receives the piston end 156 of the plunger assembly 150. The inner wall has a substantially unchanging inner diameter DB along its length. The piston 156 has an approximately similar diameter to that of the wall 212. The piston 156 can define a smooth edge that provides a low-friction, substantially fluid-tight seal with the inner wall 212. Alternatively, the piston 156 can include additional sealing members (O-rings for example).

The plunger assembly includes a proximal-most thumb plate 220, which is pressed upon distally (arrow 142) by the practitioner to deliver the injection, while gripping the barrel 130 with at lest two other fingers, braced against the flange 210. When the thumb plate is depressed, it generates a force and pressure on the plunger assembly 150, which is resisted mainly by the resistance to flow of the fluid within the barrel 130. The plunger assembly 150 comprises a main operative component of the novel safety syringe according various embodiments of this invention. The movably interconnected proximal section 152 and distal section 154 of the plunger assembly 150 collectively provide an immediate tactile indicator of an injection pressure in excess of the maximum injection pressure based upon relative movement between these sections in a longitudinal (parallel to arrow 142) direction under sufficient pressure therebetween. More particularly, the proximal end of the piston-containing distal section 154 includes a plurality of wedge-shaped ramps 230, 232 and 234 arranged as steps along the longitudinal direction. In this embodiment, each ramp has a similar size and shape, with the ramp face 240 being disposed at a non-perpendicular angle AR with respect to the longitudinal direction. The bottom of each ramp 230, 232, 234 includes a shoulder 242 that extends at an approximately perpendicular angle. The proximal-most ramp 230 is capped by a shoulder formed by an overlying plate 250. The ramps 230, 232, 234 can each extend around the entire circumference of the distal section 154, or can be circumferentially segmented, and placed at locations where needed to receive resilient, distally extended ratchet arms on the proximal section 152 of the plunger assembly 150.

The ratchet arms 270 are so named because they each include a distal pawl or spur 272 that is shaped to conform to the shape of each ramp 230, 232, 234. The ratchet arms 270 extend from a proximal base 274, and each have a thickness TA in the radial direction that enables elastic deformation/bending within the predetermined range. In a resting state, the arms take the form depicted in FIG. 2 wherein the pawls 272 are firmly nested against the corresponding ramp. In this manner each pawl is captured by the corresponding ramp and the overall plunger 150 assembly is defined by the two engaging sections 152, 154.

The combination of the proximal section's (152) modulus of elasticity and spring constant, the thickness TA of the arms 270 and the radial depth and angle AR of the ramps 230, 232, 234 and length LA of the arms 270 combine to define a degree of force applied to the distal section that will overcome the engagement between the pawls 272 and the corresponding ramp, and jump to the next, more distal ramp. That is, each arm is a leaf spring, unitarily molded as part of the proximal section. The ramps and pawls are inclined planes. When a sufficient longitudinal force is applied to the proximal section against resistance in the distal section 154, the longitudinal force is resolved into vectors that allow the arms to be flexed/elastically deformed. Hence the pawls can move distally relative to the adjacent ramps and allow them to jump from the current ramp onto the next ramp in a highly noticeable, ratcheting manner.

In this embodiment, the portion of the distal section 154 that is proximal of the piston 156 has a relatively constant diameter DDP along its length. This diameter is less than the inner diameter DB of the barrel 130. Within the barrel, near the distal tip resides an internal stop 260. This stop projects inwardly a predetermined distance sop as to define smaller inner diameter DS. The stop 260 can be molded into the syringe or applied subsequent to formation of the barrel 130. It can be a circumferential ring or a segmented structure. In particular, the diameter DDP is defined so that the distal section 154 can clear the inwardly projecting stop 260 with the stop inner diameter DS equal-to, or slightly greater than, the distal section diameter DDP. Moreover, the diameter DRA of the proximal section 152 (including the ratchet arms when unflexed and captured in one of the ramps 230, 232, 234) DRA is less than or equal to the stop diameter DS. The inner diameter DPP between the arms 270, and within a cavity 280 (shown in phantom) proximally above the arms is smaller than the distal section diameter DDP. Likewise, the maximum diameter of the first two ramps 230, 232 and the 250 conform to the smaller diameter DPP so that the arms are unflexed, and can clear the stop 260, as the plunger 150 passes down the barrel 130.

Figure 3:
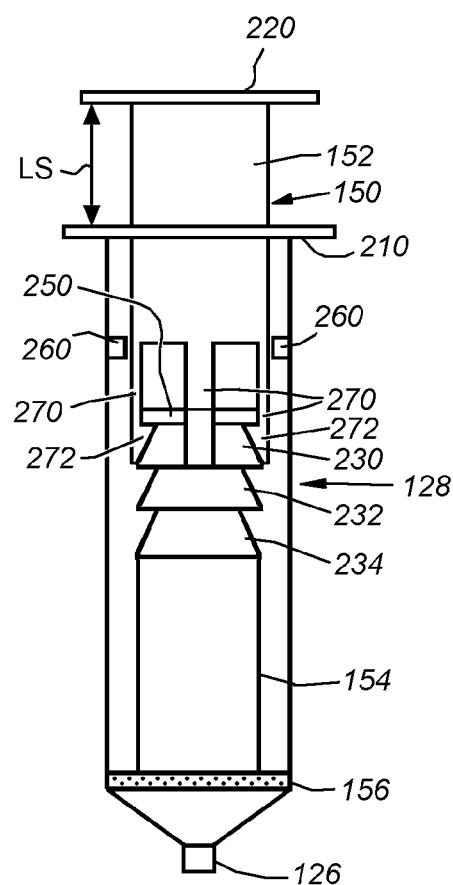
FIG. 3 is an exposed side view of the safety syringe as shown in FIG. 2, with the plunger assembly located in a position subsequent to the successful administration of an injection on the first attempt thereof.

Accordingly, as shown in FIG. 3, when the plunger assembly is pressed (arrow 142), and the resistance of the fluid does not generate back pressure in excess of the maximum pressure (20 psi in one example), the ratchet arms do not flex sufficiently to ride over the first ramp, and the plunger 150 assembly, as a unit drives the piston 156 completely to the bottom of the barrel 130. Thus, the syringe of FIG. 3 represents an acceptable completed injection procedure in which no potentially dangerous levels of injection pressure were encountered. Note that the thumb plate 220 is spaced apart from the flange 210 when the injection is completed. This is because the overall length LDP (FIG. 2) of the proximal section 152 between the plate 250 and the piston 156 is sufficient to leave an exposed length LS of the section. This length is needed to complete the injection if the plunger assembly is forced to ratchet once or twice during the injection procedure.

Figure 4:
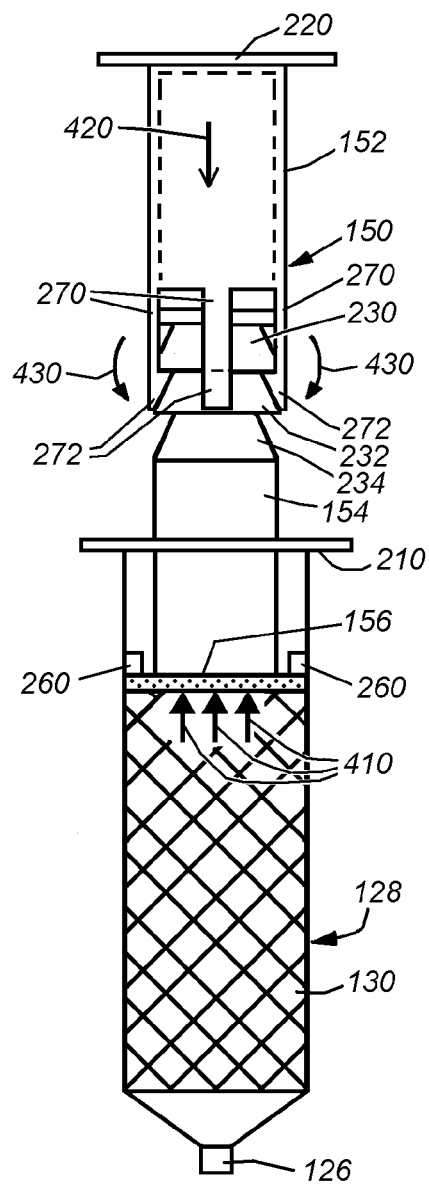
FIG. 4 is an exposed side view of the safety syringe as shown in FIG. 2, with the plunger assembly located in a position prior to administration of an injection following a first unsuccessful attempt in which a predetermined injection pressure is exceeded.
Figure 5:
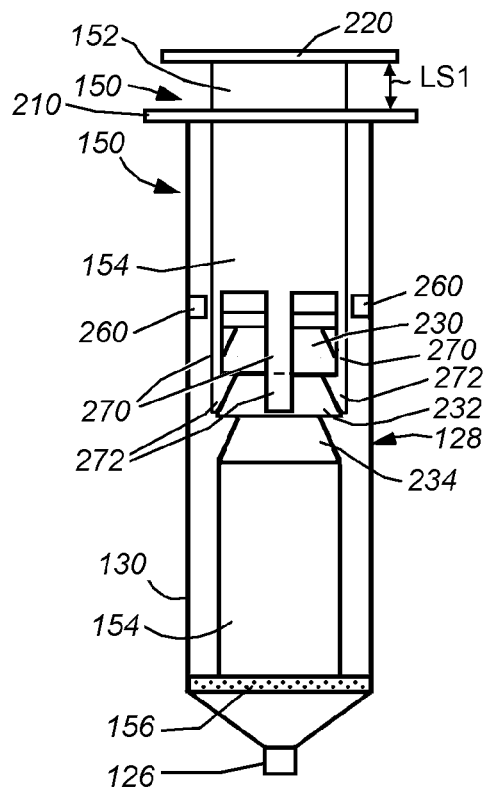
FIG. 5 is an exposed side view of the safety syringe as shown in FIG. 4, with the plunger assembly located in a position subsequent to the successful administration of an injection.

Such a ratcheting action is shown in FIG. 4, in which the practitioner has encountered an excess back pressure in the fluid (arrows 410) bearing upon the piston 156 as the plunger assembly 150 is driven distally (arrow 420). The excess pressure has caused the spring force of the arms 270 to be overcome, making then slip off the proximal-most ramp 230, and onto the next ramp 232 (curved arrows 430). It is assumed that this slippage and the clearly felt click as the pawls 272 seat within the next ramp 232 will be sufficient to alert the practitioner of the use of excess pressure, and possibly the need to manipulate the location of the needle further to avoid a nerve interior or other problematic location. Assuming the needle is properly manipulated subsequent to the ratcheting event, or injection pressure is otherwise reduced, then the remainder of the injection procedure can be completed as shown in FIG. 5. In this case, the distance LS1 between the flange 210 and the thumb plate 220 has been reduced by the movement onto ramp 232. The distance LS1 is less than the distance LS of FIG. 3, but still provided sufficient clearance to complete the injection and allow for further ratcheting if needed.

Figure 6:
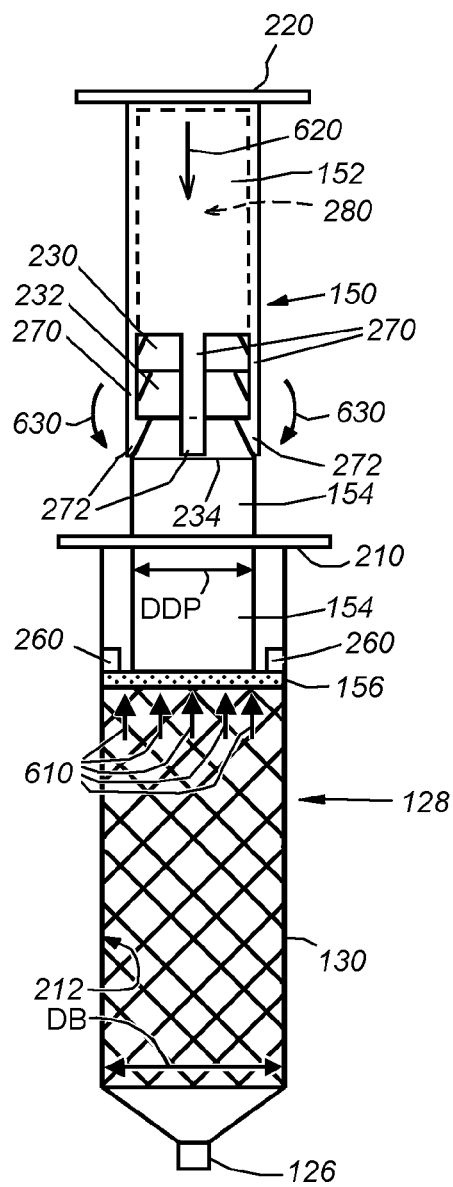
FIG. 6 is an exposed side view of the safety syringe as shown in FIG. 2, with the plunger assembly located in a position prior to administration of an injection following a second unsuccessful attempt in which the predetermined injection pressure is exceeded.

Such additional ratcheting is shown in FIG. 6, in which the practitioner has yet again encountered excess backpressure (arrows 610) as the plunger assembly 150 (already ratcheted to ramps 232) is driven distally (arrow 620). The excess pressure has again caused the spring force of the arms 270 to be overcome, making then slip off the central/second ramp 232, and onto the next, distal-most ramp 234 (curved arrows 630). It is again assumed that this slippage and the clearly felt click as the pawls 272 seat within the next ramp 232 will be sufficient to alert the practitioner of the use of excess pressure, and possibly the need to even further manipulate the location of the needle to avoid a nerve interior or other problematic location. Note that, while the ratcheting action is shown occurring at the initiation of the injection procedure, it may also occur during the course of plunger movement. So long as the stop 260 and the arms 270 are arranged to prevent interference too early in the process, the arms are free to ratchet even as the plunger piston 165 has moved some distance into the barrel 130. Once the arms move over the stop, they may be restricted from flexing. However, it is assumed that the injection has mostly succeeded before the arms become restricted from flexing. As will be described below, it is expressly contemplated that alternate ratcheting or slippage mechanisms can be employed that are not limited by a stop.

Figure 7:
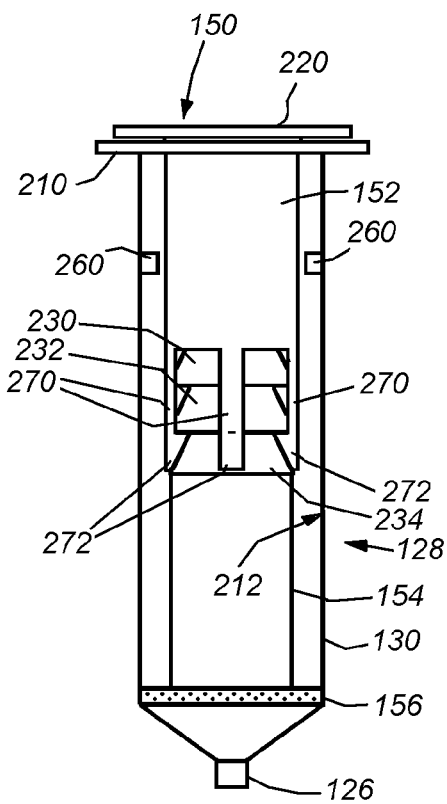
FIG. 7 is an exposed side view of the safety syringe as shown in FIG. 6, with the plunger assembly located in a position subsequent to the successful administration of an injection.

Assuming the second injection attempt is eventually completed successfully, then the syringe assumes the orientation depicted in FIG. 7. In this embodiment, minimal clearance remains between the thumb plate 220 and the barrel flange 210. This is because the practitioner has been provided his or her last chance to perform the injection properly.

As shown in FIG. 8, the practitioner has again exceeded excess backpressure (arrows 810) during his or her attempt to drive (arrow 820 the plunger assembly distally. The pawls 272 have, thus, jumped over the last ramp 234 (curved arrows 830), and are no longer captured by a more distal ramp. Rather the arms 270 become spread and elastically flexed radially outwardly as shown. The radial thickness of the pawls 272, combined with the diameter DDP of the distal section 154 locate the ends of the arms at a radial spacing that practically matches the inner diameter DB and ensures the arm ends will not pass the stop. In addition the proximal section's upper cavity 280 has a diameter and longitudinal length sufficient to receive the distal section 154 thereinto as shown in phantom in FIG. 8. Hence, with relatively little resistance, the pawls slide along the distal section as shown, without driving the distal section against the backpressure 810. Eventually, as shown in FIG. 9, the proximal end of the distal section 154 is completely enveloped by the cavity 280, and the proximal section 152 can move no further due to interference between the arm ends and the stop 260. At this point the syringe is locked against further injection.

Of course in the illustrative embodiment, the practitioner can withdraw the proximal section 152 proximally to place the pawls 272 back onto (at least) the distal-most ramp 234 and try again, but in any event a potentially crippling injection procedure has been effectively avoided, and cannot be completed, regardless of the number of attempts, until the backpressure is reduced. In alternate embodiments, an additional locking structure can prevent withdrawal of the proximal section at all, once it has finally failed as shown in FIG. 9. For example, such a locking structure can include one or more notches located adjacent to the distal end of the straight section of the distal portion that capture corresponding arm pawls after they slide distally over the straight section to the stop.

Figure 10:
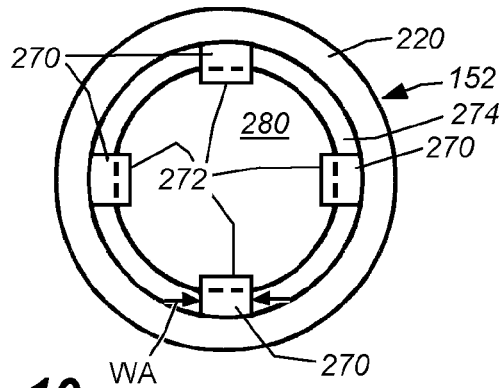
FIG. 10 is a bottom view of the proximal section of the plunger assembly of the safety syringe, including four ratchet arms disposed at 90-degree intervals about the perimeter, according to an illustrative embodiment.

In the illustrative embodiment of FIGS. 2-9, the proximal section 152 includes four circumferentially spaced arms 270. The layout of the arms 270, as well as other components, is further detailed in the bottom view of FIG. 10. The individual arms can have a width WA that is highly variable. This width dimension, as well as the length LA of the arms and the thickness TA collectively define the spring constant. One or more dimension can be altered to adjust the resistance pressure. Likewise the number of arms employed and their placement can affect the resistance force.

Figure 11:
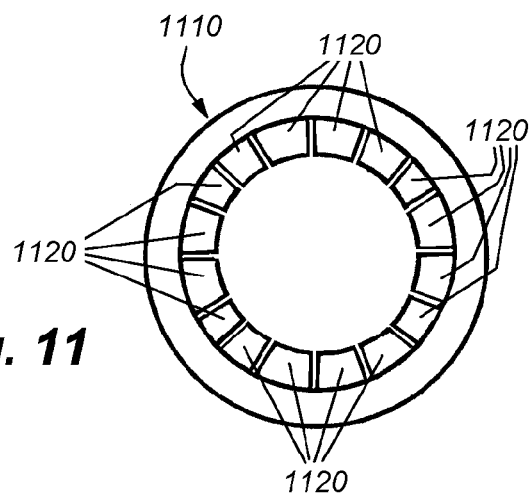
FIG. 11 is a bottom view of a proximal section of the plunger assembly of a safety syringe according to an alternate embodiment, including a multiplicity of, adjacent closely spaced ratchet arms disposed about the perimeter.

An alternate embodiment of a proximal section 1110 of a plunger assembly that can be employed with the above-described distal section 154 and barrel 130 shown in bottom view in FIG. 11. One concern with the use of a minimal number of arms is that the proximal section of the plunger assembly may not be stably supported on the distal section as it is depressed. That is, one of the arms may experience greater driving pressure than the others during depression due to uneven application of force on the thumb plate—thereby causing that leg to jump to the next ramp while the others only flex. The result would be a bent plunger assembly that would make administering the injection difficult or impossible. To provide a more stable interconnection between the proximal and distal sections, the number of arms 1120 is increased to a virtually continuous circumferential array as shown in FIG. 11. The arms 1120 are thereby divided by a relatively narrow gap.

Figure 12:
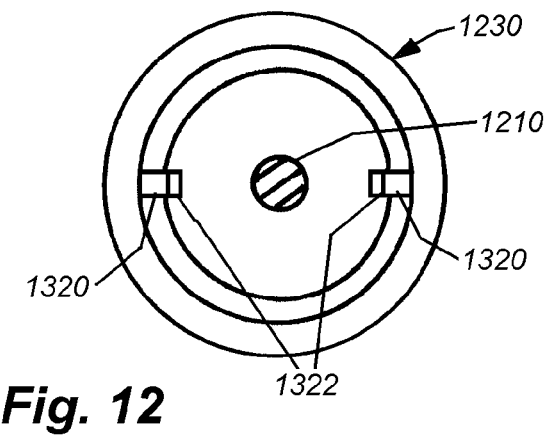
FIG. 12 is a bottom view of a proximal section of the plunger assembly of a safety syringe according to an alternate embodiment, including a central guiding rod for increased rotational stability between the proximal section and a distal section, and at least a pair of opposed ratchet arms.
Figure 13:
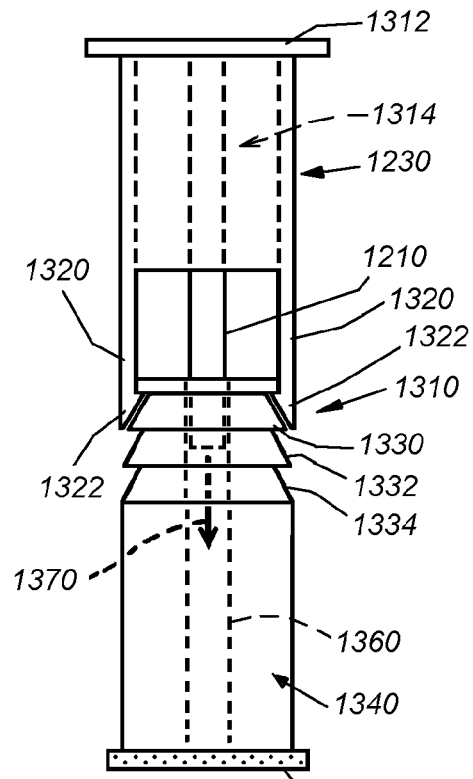
FIG. 13 is an exposed side view of the safety syringe, according to an alternate embodiment, employing the proximal section of the plunger assembly of FIG. 12.

A plunger assembly 1310 with a more-positive mechanism for ensuring an aligned transition between ratchet positions is detailed in FIGS. 12 and 13. The embodiment of FIGS. 12 and 13 includes a central guide rod 1210 attached to the interior of the thumb plate 1312 and extends through an upper/proximal cavity 1314 (shown in phantom) distally over a predetermined distance. The guide rod 1210 is surrounded at least two flexible spring arms 1320 with associated pawls 1322 mounted on a proximal section 1230. The pawls 1322 move in a ratcheting manner distally as the maximum pressure is exceeded over ramps 1330, 1332 and 1334 in the distal section 1340. The distal section 1340 includes a cylindrical distal portion that terminates in an appropriately sized piston 1350, which conforms to the inner diameter of the associated syringe barrel (not shown). The distal section 1340 also includes a conforming central channel 1360 (shown in phantom) that receives the central guide rod 1210 as the proximal section 1230 is ratcheted and/or disconnects to lock-up the syringe (dashed arrow 1370). The central guide rod 1210 and channel 1360 collectively resist misalignment or bending of the proximal section 1230 with respect to the distal section 1340 as it ratchets between ramps. Other functions are in accordance with the description of the embodiment of FIGS. 2-10 above. Note that the guide rod 1210 and channel 1360 can be formed in a polygonal, or more-complex geometrical shape (for, example cruciform) so that relative rotation of the distal and proximal sections is resisted. Likewise, the number of arms is highly variable, as is their placement. More generally, this embodiment contemplates that a slidable member interengages the two plunger assembly sections so as to resist bending therebetween, while a ratcheting component that interacts between the sections provides for a tactile signal between multiple attempts to inject, along with a final lock-up of the syringe.

Figure 14:
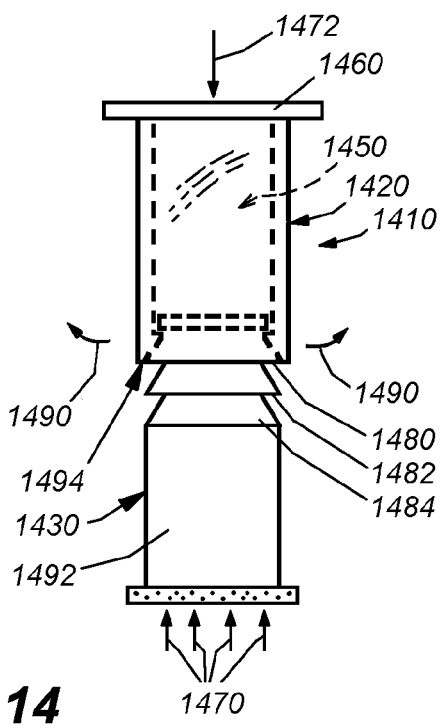
FIG. 14 is an exposed side view of a plunger assembly for a safety syringe according to another alternate embodiment, including a proximal section having a resilient ratchet lip that flexes in response to induced hoop stress so as to move with respect to an attached distal section.
Figure 15:
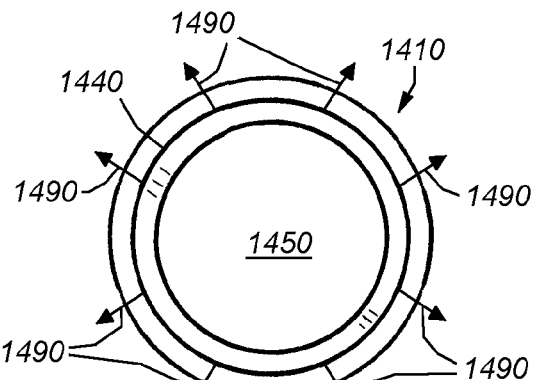
FIG. 15 is a bottom view of the proximal section of the plunger assembly of FIG. 14 detailing an induced hoop stress along the perimeter of the ratchet lip.

Another alternate embodiment of ratcheting plunger assembly 1410 for use in a safety syringe (having a syringe barrel (130) as generally described herein) is detailed in FIGS. 14 and 15. This plunger assembly 1410 includes a proximal section 1420 and an interengaging distal section 1430 that operate to ratchet and lock-up the syringe generally in conformance with the principles described herein. The distal section 1420 includes a circumferential pawl structure 1440 that extends into the distal end of a cavity 1450 (and terminates at the inner side of the thumb plate 1460). When the backpressure (arrows 1470) provides resistance to downward injection pressure (arrow 1472) in excess of the maximum injection pressure, the ramps 1480, 1482, 1484 induce a radial hoop stress (arrows 1490) on the pawl rim that is sufficient to elastically deform the rim sufficiently so that it can jump between ramps to thereby ratchet the plunger assembly 1410. The material and/or dimensions of the proximal section 1420 afford sufficient elasticity so that the continuous rim of the pawl rim structure 1440 can jump to the next ramp and/or the continuous-diameter, cylindrical-portion 1492 of the plunger's distal section 1420 in response to pressure in excess of the maximum injection pressure. After three attempts (in this embodiment) toward a successful injection, the pawl rim structure 1440 rides onto the continuous portion 1492, thereby providing a disconnect between the proximal section 1420 and the distal section 1430, which provides the requisite lock-up of the syringe so as to prevent overpressure in the injection procedure. The materials of the plunger assembly's sections should be sufficiently non-frictional in engagement so that the practitioner's distal driving action (arrow 1472) of the hoop-stressed rim 1440 still overcomes the backpressure (arrows 1470) of the fluid. Hence, the pawl rim structure 1440 can effectively override the distal, cylindrical portion 1492, thereby causing the radially outwardly deformed distal end 1494 of the rim 1440 to engage the barrel's stop (not shown, but equivalent to the stop 260 above) if three attempts are failed—thereby locking-up the syringe in a manner described above.

It is expressly contemplated that the ratcheting mechanism that provides both a direct, immediate tactile feedback to the practitioner and the ability to lock-up the injection procedure in the event of one or more over-pressure events can be constructed in a variety of manners. In general, the plunger assembly provides the ratcheting and lock-up functionalities herein. In various embodiments, as described above, the syringe barrel is modified from a relatively conventional design to include a stop structure (260) that can be omitted where the safety syringe is directed mainly toward a tactile indicator of overpressure, or provides an alternate lock-up mechanism. Of course, in alternate embodiments, the barrel can be further modified to include other aspects of thee ratcheting and/or lock-up mechanisms.

Figure 16:
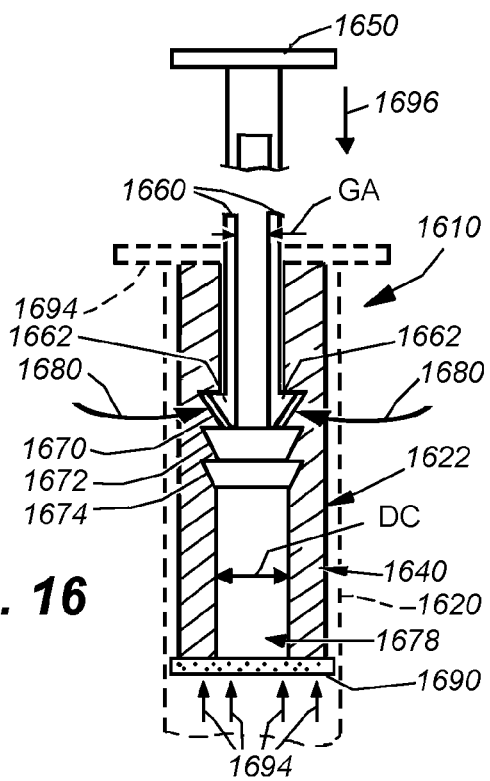
FIG. 16 is a partial side cross section of a safety syringe, providing an internal ratcheting mechanism according to a further alternate embodiment of this invention.

FIG. 16 depicts a partial view of a safety syringe 1610 according to a further embodiment of the invention in which the barrel 1620 (shown in phantom) is free of an internal stop or other modifications with respect to convention syringe barrel designs. This allows the barrel to remain substantially unmodified, thereby reducing complexity and production costs. This arrangement also potentially eases assembly concerns since the plunger assembly 1622 can be slid into the completed safety syringe unit without concern for the obstruction of an internal stop assembly within the barrel.

As depicted, the plunger assembly 1622 consists of a proximal section 1630 and a distal section 1640. The proximal section includes a thumb plate 1650 that is attached to a plurality of circumferentially separated ratchet arms 1660. The ratchet arms 1660 each carry a radially outwardly extended pawl 1662 at a distal-most end thereof. The pawls 1662 conform to a set of stepped ramps 1670, 1672, 1674 that extend toward a narrowed channel 1678, terminating adjacent to a piston 1690 residing at distal-most end of the distal section 1640. The arms 1660 flex radially inwardly (curved arrows 1680) in response to a predetermined pressure differential (between proximally directed fluid backpressure (arrows 1694) and distally directed injection driving force (arrow 1696) to jump from one ramp to another as the maximum injection pressure is exceeded. The radial gap GA between the arms 1660 is sufficient to allow such flexure and enable the pawls 1662 to override the ramps 1670, 1672, 1674. The diameter DC of the channel 1668 is also defined so that the arms 1660 can be fully inwardly flexed, and ride distally into the channel 1678. By appropriate sizing and arranging of the proximal and distal sections 1630 and 1640, respectively, the thumb plate 1650 engaged to proximal/top end 1694 of the barrel 1620 before the distal ends of the arms 1660 bottom-out within the channel 1678. Thus, the plunger assembly 1622 provides the requisite lock-up function subsequent to a predetermined number of injection attempts (three attempts in this embodiment). The lock-up is achieved completely within the plunger assembly 1622, thereby allowing it to be employed universally within a variety of standard-sized syringe barrels. In this embodiment, the combination of the barrel's proximal end and the thumb plate can be defined as the "stop" that prevents the injection from occurring after the distal and proximal sections are disconnected by the ratcheting mechanism.

In this embodiment, and others described herein, one or more of the components of the safety syringe and/or plunger assembly can be provided with a discrete indicia, such as color-coding, to identify the relevant application of the safety syringe (e.g. neural block, ocular, etc.) and/or the maximum allowable injection pressure permitted by the assembly.

It should be clear to those of ordinary skill that a safety syringe according to the various embodiments described herein affords the practitioner a highly discernable and immediate tactile feedback to any condition in which a maximum safe injection pressure is exceeded using a ratcheting mechanism. This mechanism also allows for multiple injection attempts after readjusting the orientation of the needle within the patient. In addition, the mechanism enables to provision of a final attempt, in which further attempts are blocked. More particularly, a lock-up function in which the plunger components become disconnected, positively prevents an over-pressurized injection (following one or more attempts) by disconnection movable components that interface the practitioner's hand with respect to the fluid piston.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, it is expressly contemplated that the lock-up function and/or the tactilely stimulating ratcheting function can be separately provided in a safety syringe according to alternate embodiments of this invention. In alternate embodiments, a single injection attempt can result in lock-up and/or the syringe can afford a plurality of ratcheting attempts without an eventual lock-up of the injection function. The ratcheting mechanism can also be implemented in a variety of manners, some of which may include additional moving parts, such as individually spring-loaded bearings mounted on the arms or another base. The pawls can define an alternate shape, such as a curvilinear outline, which conforms to a conforming curvilinear ramp shape. In addition, while the moving component is provided within the proximal section of the plunger assembly in the various illustrative embodiments shown and described herein, the moving component(s) can be provided within the distal section, within a combination of the distal and proximal sections, or within both sections—and also within the barrel where appropriate. Based upon the foregoing description, such implementations should be within the purview of those of ordinary skill in the art. Accordingly, this description is meant to be taken only by way of example, and not to otherwise limit the scope of this invention.

What is claimed is:

1. A safety syringe comprising:
   a barrel that contains a predetermined volume of fluid, and having an inner wall, a proximal end, a distal end and a longitudinal axis;
   a plunger assembly including a proximal plunger section having proximal and distal ends, and an interconnected distal plunger section having proximal and distal ends;
   the distal plunger section including a piston at the distal end of the distal plunger section and that provides a substantially fluid-tight slidable seal with respect to the inner wall of the barrel;
   the proximal plunger section including, at the proximal end thereof, a cavity for matingly receiving the proximal end of the distal plunger section for relative motion therebetween;
   a ratcheting mechanism constructed and arranged to provide a tactile feedback in response to direction of the piston against the fluid so as to generate a backpressure in excess of a predetermined maximum pressure, the tactile feedback being provided each of a predetermined number of times;
   the ratcheting mechanism including a plurality of wedge-shaped ramps constructed and arranged as steps in a direction of the longitudinal axis and disposed at the proximal end of the distal plunger section;
   the ratcheting mechanism further including at least one ratchet arm that is peripherally disposed and extends distally at the distal end of the proximal plunger section;
   the ratchet arm including a distal pawl for conforming engagement with a corresponding wedge-shaped ramp;
   a thumb plate disposed at the proximal end of the proximal plunger section; and
   a stop secured to the inner wall of the barrel forming a projection against which a distal pawl end of the ratchet arm engages subsequent to disconnection of the distal plunger section from the proximal plunger section.

2. The safety syringe as set forth in claim 1 wherein the ratcheting mechanism is constructed and arranged to disconnect the distal plunger section from the proximal plunger section so as to prevent the proximal plunger section from directing force to the piston after the predetermined number of times.

3. The safety syringe as set forth in claim 2 wherein the distal plunger section includes a distal portion disposed between the piston and ramps, a distal-most of the ramps being constructed and arranged to direct the ratchet arm into the distal portion so as to disconnect the distal plunger section from the proximal plunger section.

4. The safety syringe as set forth in claim 3 wherein the projection comprises an annular projection.

5. The safety syringe as set forth in claim 1 further comprising a guide rod that maintains a bend-free alignment between the proximal plunger section and the distal plunger section.

6. The safety syringe as set forth in claim 1 wherein the at least one ratchet arm includes a continuous rim that flexes under hoop stress in response to a predetermined pressure.

7. The safety syringe as set forth in claim 1 wherein the distal plunger section includes a distal portion disposed between the piston and ramps, and wherein the proximal plunger section includes a plurality of ratchet arms, the ratchet arms engaging with the distal portion when an excess back pressure is reached.

8. The safety syringe as set forth in claim 7 wherein, when the ratchet arms ride over the distal portion, the ratchet arms are constructed and arranged to engage with the stop to inhibit further motion of the proximal plunger section.

9. The safety syringe as set forth in claim 8 wherein the projection comprises an annular stop having an inside diameter that is greater than a diameter of the distal portion so that when the pawl engages a ramp the proximal plunger section passes the annular stop.

10. The safety syringe as set forth in claim 9 wherein the ratchet arms comprise four disposed in a diametric pattern.

11. A safety syringe comprising:
    a barrel that contains a predetermined volume of fluid, and having an inner wall, a proximal end, a distal end and a longitudinal axis;

a plunger assembly including a proximal plunger section having proximal and distal ends, and an interconnected distal plunger section having proximal and distal ends;

the distal plunger section including a piston at the distal end of the distal plunger section and that provides a substantially fluid-tight slidable seal with respect to the inner wall of the barrel;

a ratcheting mechanism constructed and arranged to provide a tactile feedback in response to direction of the piston against the fluid so as to generate a backpressure in excess of a predetermined maximum pressure, the tactile feedback being provided each of a predetermined number of times;

the ratcheting mechanism including a plurality of wedge-shaped ramps constructed and arranged as steps in a direction of the longitudinal axis and disposed along the distal plunger section;

the ratcheting mechanism further including at least one ratchet arm that is peripherally disposed and extends distally at the distal end of the proximal plunger section;

the ratchet arm including a distal pawl for conforming engagement with a corresponding wedge-shaped ramp; and a thumb plate disposed at the proximal end of the proximal plunger section.

12. The safety syringe as set forth in claim 11 including a stop secured to the inner wall of the barrel forming a projection against which a distal pawl end of the ratchet arm engages subsequent to disconnection of the distal plunger section from the proximal plunger section.

13. The safety syringe as set forth in claim 12 wherein, when the ratchet arm rides over the distal portion, the ratchet arm is constructed and arranged to engage with the stop to inhibit further motion of the proximal plunger section.

14. The safety syringe as set forth in claim 11 wherein the wedge-shaped ramps are disposed on an outer surface of the distal plunger section and the pawl extends inwardly to engage a ramp.

15. The safety syringe as set forth in claim 14 wherein the distal plunger section includes a distal portion disposed between the piston and ramps, and wherein the proximal plunger section includes a plurality of ratchet arms, the ratchet arms engaging with the distal portion when an excess back pressure is reached.

16. The safety syringe as set forth in claim 11 wherein the wedge-shaped ramps are disposed within a channel of the proximal plunger section and the pawl extends outwardly to engage a ramp.

* * * * *